United States Patent [19]

Deindoerfer et al.

[11] Patent Number: 4,476,231

[45] Date of Patent: Oct. 9, 1984

[54] METHOD OF ANALYZING THE DISTRIBUTION OF A REAGENT BETWEEN PARTICLES AND LIQUID IN A SUSPENSION

[75] Inventors: Fred H. Deindoerfer, Northridge; James R. Gangwer, Chatsworth, both of Calif.

[73] Assignee: International Remote Imaging Systems, Inc., Chatsworth, Calif.

[21] Appl. No.: 286,027

[22] Filed: Jul. 22, 1981

[51] Int. Cl.³ .................... G01N 33/54; G01N 33/56
[52] U.S. Cl. .................................... 436/534; 356/39; 382/6; 436/800; 436/804; 436/805
[58] Field of Search ............... 436/500, 533, 534, 800, 436/804, 805; 356/39; 382/6; 377/10, 11

[56] References Cited

U.S. PATENT DOCUMENTS

| | | | |
|---|---|---|---|
| 3,088,875 | 5/1963 | Fisk | 167/84.5 |
| 3,247,078 | 4/1966 | Herrett | 195/102 |
| 3,492,396 | 1/1970 | Dalton et al. | 424/12 |
| 3,520,609 | 7/1970 | Lion | 356/39 |
| 3,794,467 | 2/1974 | Adams et al. | 23/230 R |
| 3,925,018 | 12/1975 | Saunders | 23/230 |
| 4,000,252 | 12/1976 | Kosak | 436/804 X |
| 4,097,845 | 6/1978 | Bacus | 356/39 X |
| 4,197,088 | 4/1980 | Meserol et al. | 356/39 X |
| 4,318,886 | 3/1982 | Kawahara et al. | 356/39 X |
| 4,338,024 | 7/1982 | Bolz et al. | 356/23 |

FOREIGN PATENT DOCUMENTS 2040441 8/1980 United Kingdom .

*Primary Examiner*—Arnold Turk
*Attorney, Agent, or Firm*—Limbach, Limbach & Sutton

[57] ABSTRACT

In an immunoassay procedure, an analyte in a solution is reacted with a reagent with a label. The reagent is segregated into solid phase (particles) and liquid phase (liquid) with the unreacted reagent ion one phase and the reacted reagent in another phase. An image of the suspension is then taken. The image is converted into electrical signal representation and is stored in digital form. The image is processed by locating and quantifying the labels. The distribution of the labels is representative of the distribution of the reagent between the particles and the liquid.

12 Claims, 4 Drawing Figures

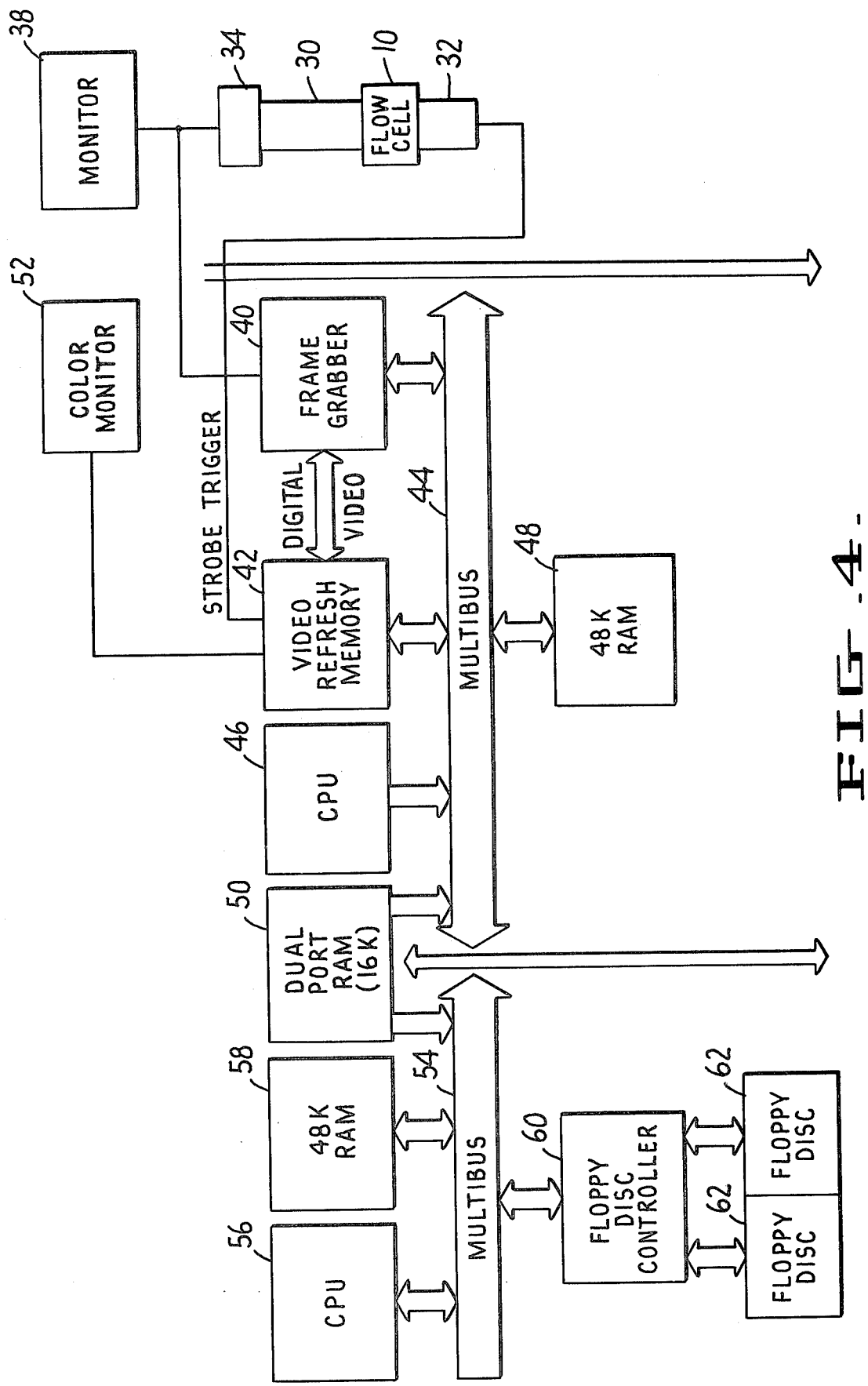

METHOD OF ANALYZING THE DISTRIBUTION OF A REAGENT BETWEEN PARTICLES AND LIQUID IN A SUSPENSION

BACKGROUND OF THE INVENTION

The present invention relates to a method of analyzing the distribution of a reagent, following its reaction, between particles and liquid in a suspension and, more particularly, wherein said analysis does not require the separation of the particles from the liquid in order to measure the distribution of the reagent.

As used hereinabove and hereinafter, the following words have the following meaning associated therewith:

Analyte—the substance in a solution which is being analyzed, its concentration is unknown and is to be determined by the assay procedure.

Reagent—a substance specifically chosen to react only with the analyte in the assay procedure.

Label—a composition of the reagent, attached thereto, allowing for its detection by a measuring means.

Distribution of label—the classification of the reagent into reacted and unreacted portions.

Segregation of label—the classification made to occur between a solid and a liquid phase usually by chemical means.

Suspension—a mixture of particles (solid phase) and liquid.

Separation of label—the actual separation of particles and liquid by physical means.

Distribution of a reagent, following its reaction between particles and liquid in a suspension, is common in clinical chemistry. Examples of such distributions occur in radio-immuno assay and fluoro-immuno assay procedures. In both of these procedures, the concentration of an analyte in solution must be determined. A reagent, having a label attached thereto, is chosen to react specifically with the analyte. Following the reaction of the reagent with the solution, a portion of the reagent remains unreacted, while another portion of the reagent has reacted with the analyte. The reacted reagent is then segregated from the unreacted reagent causing a distribution thereof, usually by causing one of the reagents (reacted or unreacted) to enter into the solid phase, while the other remains in liquid phase. For example, this may occur by adsorbing either the reacted or unreacted reagent on a solid phase substance such as antibody coated beads, or charcoal, or precipitating the reacted reagent by the addition of precipitate causing substances such as polyethyleneglycol or second antibodies. A suspension of reacted and unreacted reagents then occurs. This suspension must be physically separated into the solid phase and the liquid phase causing a separation of the reacted reagent portion from the unreacted portion. Once the separation is made, then the measurement of each separate portion can be made. The label which is associated with the reagent is typically a radioactive isotope in the case of radio-immuno assay and is a fluorescent material in the case of fluoro-immuno assay. Other labels may also be used. The reagent is chosen such that its reaction and subsequent distribution is effected only by a specific analyte whose concentration is being determined. The reagent has the label attached thereto in order that its distribution may be measured, usually by emission sensing means. The portion of the reagent which distributes as determined by measuring its label, is indicative of the quantitative measure of the analyte concentration being determined by the assay procedure. In both the radio-immuno assay and fluoro-immuno assay procedures, the reacted and unreacted portions of the reagent are made to separate between two phases, either of which can be measured after they, in turn, are separated by physical means. The particle portion or the liquid portion of the suspension is analyzed to determine the quantitative measure of the label that is contained therein. In this manner, the unknown concentration, i.e., the quantitative measure of the specific analyte may be calculated. In the case of radio-immuno assay procedure, the separate particles or liquid is analyzed by converting the nuclear radiation emitted by the label into visible light by a scintillation crystal. The visible light is then detected by a photomultiplier tube. In the case of fluoro-immuno assay procedure, the separated particles or the liquid is irradiated with a beam of electromagnetic radiation, typically UV light. The amount of label present within the separated particles or the separated liquid would then fluoresce. The amount of fluoresence is then detected by a photomultiplier tube. Thus, in the case of an immuno-assay procedure, there is a reaction involving a reagent having a label, with a subsequent distribution and segregation of the reacted and unreacted portions of the reagent into solid and liquid phases. The separation and washing of these phases require intensive human handling and are a source of imprecision and error in the assay procedure.

MIA, or Microscopical Image Analysis, involves the examination of a suspension containing particles of interest in a microscope. Images of the suspension under the microscope are taken and are digitized and processed by imaging techniques in order to extract information relating to the selected components of the image which are of interest. Such an apparatus has been proposed for use to analyze particles in a suspension such as blood. U.S. patent application Ser. No. 146,064 filed on May 2, 1980 in the names of Gunner Bolz and Sherman DeForest now U.S. Pat. No. 4,338,024 and assigned to the assignee of the present application, deals with one such MIA apparatus.

SUMMARY OF THE INVENTION

Therefore, in accordance with the present invention, a method is provided for analyzing the distribution of the reacted and unreacted reagent within a suspension, wherein the suspension is a mixture of particles and liquid. The reagent has a label attached thereto. The method comprises examining the suspension by image sensing and pattern recognition means in a microscope. An image of the suspension is formed. The image is converted into an electrical signal representation. The electrical representation is stored in digital form. The image is then processed into digital form by locating and quantifying the labels. Thus, the distribution of the labels, is representative of the distribution of the reagent, between the particles and the liquid.

BRIEF DESCRIPTION OF THE DRAWINGS

FIG. 4 is a schematic diagram of the electronic processor employed by the apparatus of FIG. 1.

DETAILED DESCRIPTION OF THE DRAWINGS

The method of the present invention is practiced as follows. A reagent containing a label attached thereto is used in an immuno-assay procedure. The reagent is chosen such that, it will react with only a specified analyte, and the quantitative measure of the analyte is to be determined. The reacted and unreacted portions of the reagent are caused to segregate between particles and liquid. The suspension comprising of particles and liquid, i.e., the reacted reagent and the unreacted reagent, from the immuno-assay procedure is then examined under a microscope. By visually inspecting the field of view of the image, the number of particles may be counted. Based on the knowledge of the amount of reagent that was used in the immuno-assay procedure, the amount of reagent in liquid form may be calculated. Since the particles and liquid are physical indicia of the reagent in two different forms, i.e., a reacted form and an unreacted form, the amount of analyte which has reacted with the reagent may be calculated. Thus, the concentration of the analyte may be determined.

Figure 1:
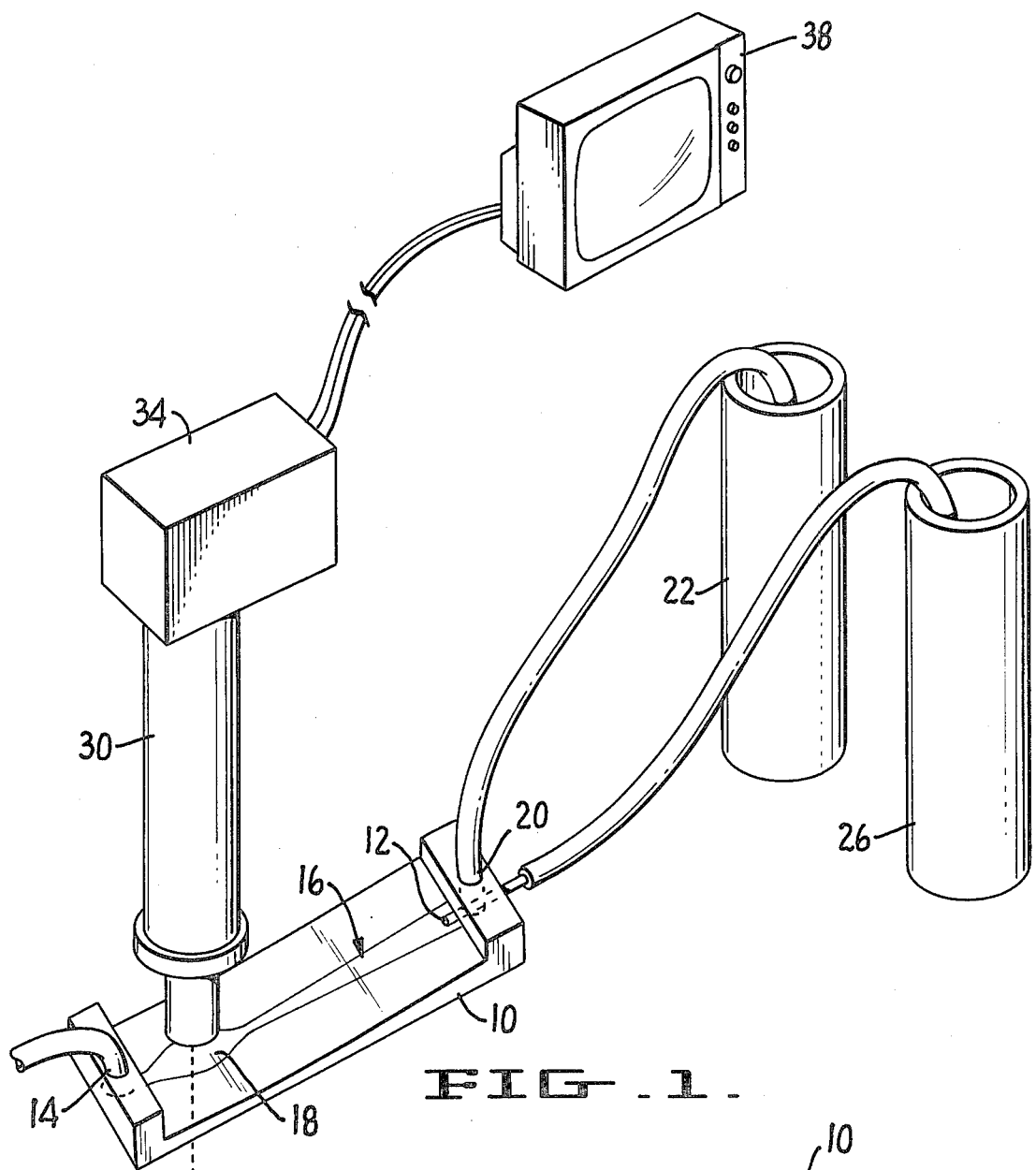
FIG. 1 is a perspective view of an apparatus adapted to perform the method of the present invention.
Figure 2:
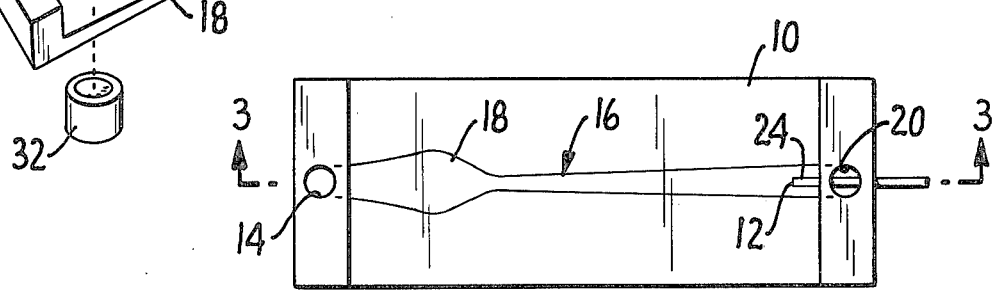
FIG. 2 is a plan view of a flow chamber of FIG. 1.
Figure 3:
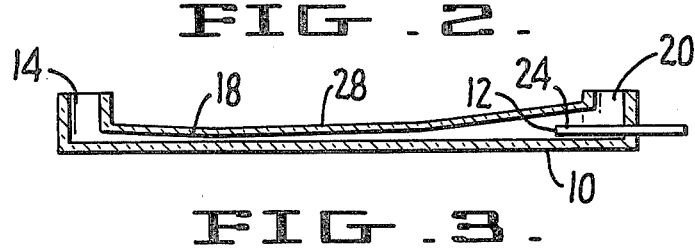
FIG. 3 is a cross sectional view of the apparatus of FIG. 2 taken on the plane indicated at 3—3.

One apparatus suitable for the method of the present invention is shown in FIG. 1. The apparatus includes a body 10 containing a flow chamber having, an inlet 12 for a suspension and an outlet 14 with a passageway 16 extending between them past an imaging area 18. The passageway 16 has an inlet with conduit 20 adapted to be connected to a volume of entraining solution 22. As illustrated in FIGS. 2 and 3, the inlet 12 for the suspension has a needle 24 in the passage way 16 downstream from the conduit 20 with a needle 24 connected to a container 26 adapted to hold the suspension to be analyzed.

A microscope 30 is focused on the examination area 18 and the examination area 18 is illuminated from below by a strobe light 32 which is preferably a U.S. Scientific Instrument Corporation model 3018 containing a 2UP1.5 lamp. The output of the microscope 30 is focused on a CCD camera 34 which is preferably a CCD camera model No. TC1160BD manufactured by RCA. The output of the CCD camera is converted to a series of still frame images, and suitable electronic processors are employed for evaluating those images. One processor which may be employed is the processor marketed as Image Analysis Systems model C-1285 by Hamamatsu Systems, Inc., Waltham, Mass. Preferably, the output of the CCD camera 34 is connected to an electronic processor 36 which is illustrated in greater detail in FIG. 4 and includes a black and white television monitor 38 and a frame grabber 40 which stores still frame images of the subject viewed by the CCD camera. The frame grabber is preferably a model FG08 frame grabber made by Matrox Corporation, Montreal, the output of which is supplied to a video refresh memory 42 model RGB 256 made by Matrox Corporation which are both coupled to the multibus 44 of the central processing unit 46, which is preferably an Intel 80/20 computer. The multibus is also coupled to a 48K random access memory 48 of Electronic Solutions Inc., and a 16K dual port random access 50 model RM 117 of Data Corporation. The output of the video refresh memory is also coupled to a color monitor 52 which may be used to provide digitally enhanced video images of individual still frames for human examination.

The second output of the dual port ram 50 is connected to a multibus 54 which is connected to an Advanced Micro Devices central processing unit 56, a 48K random access memory of Electronic Solutions, Inc. 58 and removable storage in the form of a floppy disc control 60, such as an Advanced Micro Devices model 8/8 and 2 units of Shugart Floppy Disc Storage 62.

Using the apparatus shown in FIG. 1, the suspension of particles and liquid from the immunoassay procedure is passed from the container 26 into the flow chamber via inlet 12. As the suspension passes through the examination area 18, an image of the suspension is taken. As can be seen from FIG. 2 and FIG. 3, the flow chamber has a width and thickness with the image formed at the examination area 18 in a direction substantially parallel to the thickness. The image is converted to an electrical signal by the CCD camera 34. The CCD camera 34 segments the electrical signal into a plurality of pixels. The amplitude of each pixel is digitized and stored within the 48K ram 48. The CPU processes the image into digital form by locating and quantifying the labels of the reagents seen within the image. The analysis of the distribution of labels is representative of the distribution of the reacted and unreacted reagent. The analysis is made by digital imaging, pattern recognition techniques. Such techniques are well known in the art (see for example U.S. Pat. No. 4,097,845).

The entraining solution 22 entrains the suspension 26 between two sheaths in the examination area 18. By adjusting the flow rate of the entraining solution 22, the thickness of the suspension 26 at the examination area 18 may be adjusted. This, in turn, adjusts the amount of suspension 26 seen by the CCD camera 34, which effects the particles to liquid ratio. This, in turn, adjusts the signal to noise ratio.

An example of the use of the method of the present invention to determine the amount of thyroxine $I^{125}$ in a second antibody precipitate, goat antirabbit globulin antibody, in which the rabbit globulin had reacted with the radioactive thyroxine may be seen as follows. The reagent has a label which is a radioactive isotope material and is adapted to emit a gamma ray radiation. The solution, having a reacted and unreacted reagent, in solid and liquid phase, emits gamma rays. The radioactive gamma rays from the label of the reagent impinge a scintillation crystal such as sodium iodide activated with one percent thallium, producing light pulses therefrom. A CCD camera takes an image of these light pulses which is representative of the location and the quantity of the labels within the image. The location and quantification of the labels in turn represent the amount and location of the reagents. At the same time, a microscope and the CCD camera are adapted to image the particles within the suspension. The location and number of particles and location and number of reagents in the same image would then determine the portion of the reagent which have segregated with those particles. The distribution of the reagents may then be calculated and used to determine the analyte concentration.

In another example of the method of the present invention, a fluoro-immuno assay reagent of goat anti-human immunoglobulin G antibody with a label of fluoroscein isothiocyanate is reacted with a fixed amount of immunoglobulin G accumulated on plastic microbeads to determine the concentration of immunoglobulin G in serum. The reagent reacts with the immunoglobulin G on the microbeads to form particles and reacts with the immunoglobulin G in serum and remains in liquid form. The suspension containing reacted reagent with the microbeads and reacted reagent with the serum in liquid form separated into solid (particles) and liquid form, is passed into the flow chamber through the inlet 12 and into the examination area 18. An image of the suspension with an indication of the number and location of the particles therein is taken by the microscope 30 as recorded by the CCD camera 34. Since this is a fluoro-immuno assay examination, the suspension is irradiated with radiation to cause the labels to fluoresce, i.e., to generate visible light in response to the radiation impinged thereon, typically UV light. The fluorescence of the label is also picked up by the microscope 30 and is imaged by the CCD camera. Appropriate filters are used as in a fluorescent microscope. The number and location of the labels as determined by the fluorescence which is indicative of the number and location of the reagent, along with the image of the number and location of the particles of interest help to determine the distribution of the action of the reagents with the analyte.

In the prior art the separation of the unreacted reagents from the reacted reagents is accomplished by causing a distribution between two phases and then separating the solid phase (particle) from the liquid, prior to quantification of the amount of reagents either in the solid phase or in the liquid. In the method of the present invention it can be seen that there is no need to separate the particles from the liquid of the suspension which contains the reagents of interest. The quantification of both the reagents within the liquid in the suspension, or the unreacted reagents, and the reagents which are bound to the particles, may proceed with the techniques of microscopical image analysis and a determination of the distribution of the reagents which are reacted and which are unreacted may be made without separating the particles from the liquid. Thus, the method of the present invention offers advantages in reducing human handling, imprecision and possible error arising therefrom. In addition, of course, the method of the present invention saves time in the analysis process and minimizing hazard from potentially infectious and sometimes radioactive particles.

It should be emphasized that the image of the suspension may be made on a microscopic slide or may be made in a flow chamber as shown in FIG. 1. The use of a flow chamber, of course, increases the signal to noise ratio. Further, the label may be any composition such that it may be easily detected, e.g., by visual or optical means.

What is claimed is:

1. A method of analyzing the distribution of a dissolved immuno-specific reagent between particles and liquid in a suspension, wherein said distribution is caused by an immuno reaction and said reagent has a spectrally distinguishable label, said method comprising:

forming an image of said suspension; converting said image to an electrical signal representation;
storing said electrical signal representation in digital form;
processing said image in said digital form by locating the particles and by measuring the intensity of the spectrally distinguishable labels between the particles and the liquid;
determining the distribution of the labels between the particles and the liquid; and
wherein the distribution of said labels is respresentative of the distribution of the reagent between said particles and said liquid.

2. A method of determining the amount of analyte in a solution by reacting a reagent having a label with said solution, said reagent reacting specifically with said analyte, forming a suspension composed of a mixture of two phases: particles and liquid (liquid phase) with said reagents reacted with said analyte in one phase and the unreacted reagent dissolved in the other phase, the method comprising forming an image of said suspension;
converting said image to an electrical signal representation;
storing said electrical signal representation in digital form;
processing said image by quantifying the intensity of the spectrally distinguishable labels associated with said particles or associated with said liquid; and
calculating the amount of analyte based on said quantification.

3. The method of claims 1 or 2 further comprising flowing said suspension through a flow chamber; and wherein said image formed is at said chamber.

4. The method of claims 3 wherein said label is visually detectable.

5. The method of claim 4 wherein said flow chamber has a width and a thickness and said image formed is in a direction substantially parallel to said thickness.

6. The method of claim 5 further comprising the step of adjusting the thickness of said suspension in said flow chamber to adjust the particle-to-liquid ratio where said image is formed.

7. The method of claims 1 or 2 wherein said converting step further comprising:
segmenting said electrical signal representation into a plurality of pixels; and digitizing the amplitude of each pixel.

8. The method of claim 7 wherein said label is a material adapted to fluoresce.

9. The method of claim 8 further comprising the step of
irradiating said reacted fluid to cause fluorescence by said label.

10. The method of claim 7 wherein said label is a material adapted to emit radioactivity.

11. The method of claim 8 further comprising the step of
converting said radioactivity to electromagnetic radiation.

12. The method of claim 11 wherein said electromagnetic radiation is visible light.

* * * * *